(12) United States Patent
Klinger et al.

(10) Patent No.: US 11,280,806 B2
(45) Date of Patent: Mar. 22, 2022

(54) MICRODISPENSING DEVICE AND AUTOMATIC MICRODISPENSING PROCESS (71) Applicant: FRAUNHOFER-GESELLSCHAFT ZUR FORDERUNG DER ANGEWANDTEN FORSCHUNG e.V., Munich (DE)

(72) Inventors: Michael Klinger, Nurtingen (DE); Christopher Laske, Stuttgart (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 450 days.

(21) Appl. No.: 15/673,528

(22) Filed: Aug. 10, 2017

(65) Prior Publication Data

US 2018/0067142 A1 Mar. 8, 2018

(30) Foreign Application Priority Data

Aug. 16, 2016 (DE) ...................... 10 2016 215 240.8

(51) Int. Cl.
*G01N 35/10* (2006.01)
*B41J 2/165* (2006.01)
(Continued)

(52) U.S. Cl.
CPC ............ *G01N 35/1016* (2013.01); *B01L 3/02* (2013.01); *B01L 3/0241* (2013.01); *B01L 3/5027* (2013.01); *B41J 2/16579* (2013.01); *B41J 2/2142* (2013.01); *C12M 29/00* (2013.01); *C12M 41/48* (2013.01); *G01N 35/1009* (2013.01); *G01N 35/1065* (2013.01); *B01L 2200/061* (2013.01); *B01L 2200/143* (2013.01); *B01L 2300/0654* (2013.01); *B01L 2300/0861* (2013.01); *B01L 2400/0439* (2013.01); *G01N 35/1074* (2013.01);
(Continued)

(58) Field of Classification Search
CPC .......................... A61M 5/1689; B05B 12/082; G01N 35/1016
See application file for complete search history.

(56) References Cited

U.S. PATENT DOCUMENTS 4,328,800 A 5/1982 Marx et al.
2007/0086021 A1 4/2007 Teichman
(Continued)

FOREIGN PATENT DOCUMENTS

DE 4211003 A1 10/1992
JP 2003-114104 A 4/2003
(Continued)

OTHER PUBLICATIONS

Search Report in parallel EP application EP 17 18 5313, EPO, Munich, dated Jan. 17, 2018.
(Continued)

*Primary Examiner* — Jonathan M Hurst
(74) *Attorney, Agent, or Firm* — Harness, Dickey & Pierce, P.L.C.

(57) ABSTRACT

Means and methods for dispensing small amounts of liquid from multi-channel microdispensing devices, suitable for use in automatic processing in biological assays and for the cultivation of cells and tissues, by means of optical control of the dosed liquid by specific light barrier units.

20 Claims, 8 Drawing Sheets (51) Int. Cl.
- B01L 3/02 (2006.01)
- B41J 2/21 (2006.01)
- B01L 3/00 (2006.01)
- C12M 1/00 (2006.01)
- C12M 1/36 (2006.01)

(52) U.S. Cl.
CPC ........ *G01N 2035/1018* (2013.01); *G01N 2035/1034* (2013.01); *G01N 2035/1044* (2013.01)

(56) References Cited

U.S. PATENT DOCUMENTS

| | | |
|---|---|---|
| 2009/0086190 A1 | 4/2009 | Kodama et al. |
| 2010/0265287 A1* | 10/2010 | Govyadinov ........ B41J 2/04586 347/9 |
| 2015/0116406 A1 | 4/2015 | Ward et al. |
| 2016/0031030 A1 | 2/2016 | Bergstrom et al. |

FOREIGN PATENT DOCUMENTS

| | | |
|---|---|---|
| JP | 2003-121452 A | 4/2003 |
| JP | 2005-134167 A | 5/2005 |
| JP | 2006-184161 | 7/2006 |
| JP | 2009-98117 A | 5/2009 |

OTHER PUBLICATIONS

Japanese Office Action (with translation) issued in corresponding Japanese Patent Application No. 2017-156707, dated Jul. 6, 2021.

* cited by examiner

MICRODISPENSING DEVICE AND AUTOMATIC MICRODISPENSING PROCESS

CROSS-REFERENCE TO RELATED APPLICATIONS

This application claims the benefit and priority of German Application No. 10 2016 215 240.8 filed on 16 Aug. 2016. The entire disclosure of the above application is incorporated herein by reference.

FIELD

The present invention relates to methods and means for the controlled automatic dispensing of small amounts of liquid with multi-channel microdispensing devices, suitable for use in automatic methods for biological assays and for culturing cells and tissues.

BACKGROUND

The automatic metering of small amounts of liquid by means of automatic microdispensing robots is known as such. With such systems, liquid media, so-called "biological fluids" such as cell suspensions, cell culture media, active compounds and/or test compounds, are automatically metered into target vessels or substrates. Typical applications are biological assays and automated cell and tissue culture (single cell technology, tissue engineering). For the purposes of series tests and high-throughput methods, the target vessels are usually multi-cell culture vessels, so-called microtiter or multiwell plates, which are mostly available in the SBS format. These have a regular arrangement of multiple individual vessels (wells), usually 24 or 96, on a common carrier. In known microdispensers, the individual target vessels are serially addressed via pipetting robots or, alternatively, in parallel via a plurality of juxtaposed metering channels. Each metering channel is formed by a separately controllable needle or nozzle on said microdispensing device.

The general mode of operation of such multi-channel microdispensing devices is based on the fact that the amount of liquid to be metered is displaced from the nozzle, pipette tip or needle by constant pressure or by individual pressure pulses. Thereby, a droplet or a liquid spurt or jet separates from the nozzle tip. The pipette, nozzle or needle is usually positioned above the target vessel in such a way that the drop or spurt falls vertically downwards. The I-DOT nanodosing technology ("immediate drop on demand technology", Fraunhofer Institute for Production Engineering and Automation IPA) is a high throughput process for the automatic processing of volumes ("liquid handling") in the nano- and microliter range. In this process, drops are metered directly and without contact from a, for example, 96-channel dispensing plate onto any target substrates, in particular a microtiter plate located therebelow. A 96-well microtiter plate in the SBS format, which is characterized by a small bore in the wells' bottom, serves as a dosing plate. The bore thus forms the respective dosing nozzle. The diameter of the bore is so small that the capillary pressure in the bore is higher than the hydrostatic pressure of the liquid in the well. The bore acts as a threshold valve. If the pressure in the well is increased rapidly for a short time by means of an actuator (dosing head) which can be placed on the respective corrugated pressure seal, liquid can escape from the nozzle. With a dosing head which is, for example, eight-fold in parallel, this can be repeated at a repetition rate of up to 600 Hz from a series of juxtaposed wells of the receiver by means of their corrugated plates. This allows throughputs in a volume range from approximately 10 nl to up to 100 µl.

In multi-channel microdispensing devices based on a different technology (multidrop microdispensing system, such as Multidrop™ Combi Reagent Dispenser, Thermo Scientific), adjacent parallel pipette tips or hollow dosing needles are each fed via a flexible dosing tube. Each metering hose is connected to a precise peristaltic pump with stepper motor, which precisely feeds and dosing the liquid to be dosed in the dosing tube. For example, a volume of 0.5 µl in the form of a droplet or spurt is delivered per each triggered metering step, with a repetition rate of up to 20 Hz. The convenient metering range is from 0.5 µl to approximately 5000 µl.

However, in practical application, it has now been found that irregularities and disturbances in the metering process can occur on individual dosing channels, that is the pipette or needle or nozzle, due to contamination or due to wear or material errors. In this case, it is likely that liquid drops are no longer properly formed, and drops or liquid spurts are no longer released in the ideal direction from the dosing nozzle, i.e., preferably vertically. In the extreme case, individual or several triggered doses are completely absent or the target vessel is not hit or is not completely hit. This leads to incorrect dosing. Such dosing errors can hitherto only be detected manually and, thus, only by samples of the dosing process or by checking the dosing result in the target vessel. The problem is that in automated high-throughput units such manual control is not practicable. An incorrect dosage must hitherto be taken into account as systematic uncertainty, which can significantly influence cultivation results or examination results and reduce yield and efficiency of the entire plant or impair the meaningfulness of the biological assays. Therefore, fully automatic systems are desirable, which can completely monitor and evaluate the type and quality of the liquid dosing. The deviation of the delivery angle of the liquid droplet or spurt from an ideal direction is ideally to be detected and, favorably, be quantified. Likewise, a continuous qualitative and quantitative monitoring of the liquid discharge at the dosing channels is intended to enable suitable measures during operation, without the need of manual intervention by the operator.

SUMMARY

The technical problem underlying the invention is the provision of methods and means for the automatic repeated delivery of liquid drops or liquid spurts in parallel multi-channel systems wherein the type and quality of the dispensed liquid are continuously monitored automatically and, if necessary, can be compensated for a setpoint value.

The technical problem is completely solved by providing a device for the automatic optical control of liquid drops or liquid spurts or jets metered or dispensed from multi-channel microdispensing devices having at least one, preferably only one, light barrier unit assigned to each dosing channel, i.e., dosing needle or dosing nozzle, of the microdispensing device. According to the invention, the light barrier unit consists of at least one, preferably only one, light source having an inhomogeneous beam profile and at least one, preferably only one, associated light sensor with a sensor surface on which the profiled light beam of said light source is projected. These are arranged directly on the dosing channel, specifically on a carrier. The light barrier unit is dimensioned and arranged in such a way that the profiled light beam between the light source and the light sensor runs essentially transversely to the direction of propagation, that is to the preferred direction of the liquid drops or liquid spurts emitted from the dosing channel. Furthermore, according to the invention, this profiled light beam is at least as broad in dimension, transversely to the direction of propagation, as the liquid droplet or liquid spurt to be controlled therethrough.

In the context of this invention, a "profiled light beam" having an "inhomogeneous beam profile" is understood as a cone-shaped light beam with an especially approximately Gaussian or leptokurtic intensity profile (Gaussian beam). Other intensity profiles are conceivable, but a light cone is preferred having the highest intensity in the optical axis, that is to say in the center of the conical light bundle, which drops in each case towards the edge of the light bundle. Light sources which are readily suitable for producing such a light cone are preferably selected from the group consisting of light-emitting diodes (LED) and semiconductor laser diodes. In a first variant, this is a substantially planar LED light field with a condenser lens integrated in a manner known per se, i.e., as a rule cast. In alternative embodiments, specific microlenses are provided for beam shaping to obtain the beam profiles: These are preferably selected from aspheric lenses and axicon lenses.

According to the invention, the profiled light beam projects onto a sensor surface of the opposing light sensor, which detects the entire beam profile of the incident light beam and integrates its intensity over its extent in the projection surface. The light sensor thus generates a sensor current which corresponds to the integrated beam intensity.

The liquid droplet or liquid spurt emitted penetrates the light beam of the light barrier unit arranged directly on the dosing channel, as a result of which the light sensor records a drop in the light intensity at its sensor surface illuminated with the profiled light beam. The drop in the luminous flux, that is to say the degree of shadowing at the sensor, is dependent on the position within the profiled light beam, at which the droplet or spurt interrupts it. In the preferred embodiment of a light beam with, in particular, Gaussian or comparably profiled intensity profile, the maximum shading, that is to say the maximum reduction in the luminous flux, occurs when the light beam is interrupted straight in its axis, that is to say in the center. In the preferred embodiment of the method, said maximum shading characterizes an ideal direction or a setpoint position of the dispensed liquid droplet or spurt.

Without wishing to be bound by theory, this light barrier unit permits a simple and at the same time sufficiently accurate monitoring of the position and direction of a dispensed liquid droplet or liquid spurt and the quality of the liquid discharge. The evaluation by means of a programmed evaluation unit (analog computer or digital program computer) makes it possible to evaluate the deviation of the type and quality of the liquid output from a desired ideal over the temporal change in the sensor current when the liquid drop or liquid spurt passes through the light beam. In the simplest case, this analysis is as follows: The further the liquid droplet or liquid spurt deviates from the ideal center position (ideal direction), the lower the change in the sensor current due to the shading of the shaped light cone. This functional relationship is illustrated graphically in FIGS. 7A to 7D.

Figure 10A:
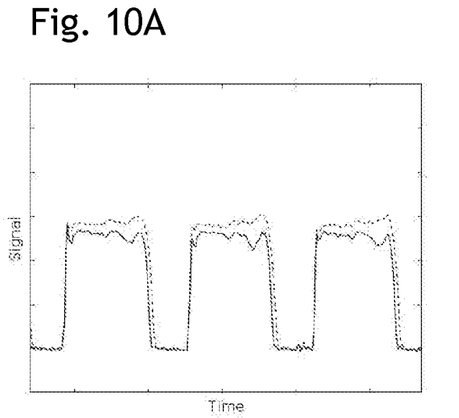
FIGS. 10A-10D graphically illustrate measured electrical signals analogously to FIG. 9.
Figure 10B:
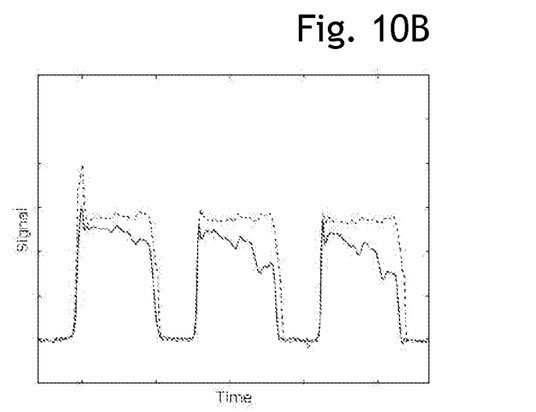
Figure 10C:
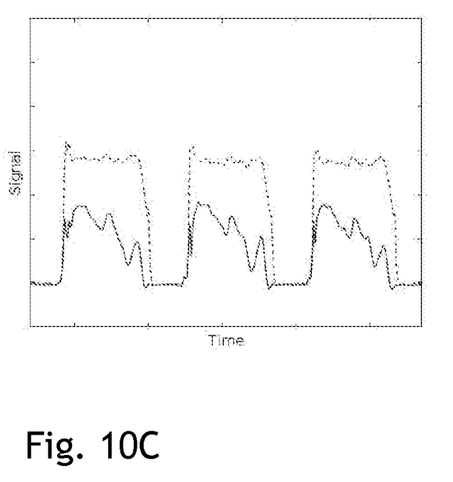
Figure 10D:
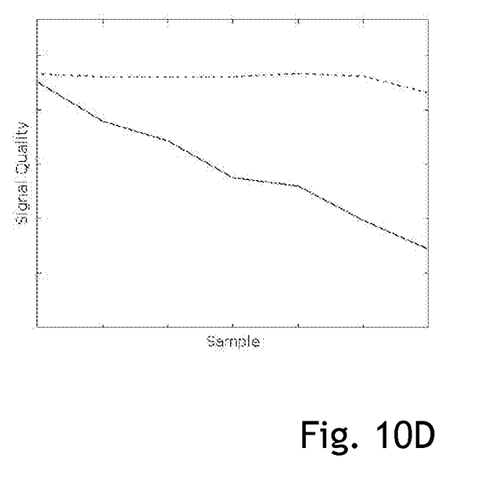

At the same time, the arrangement according to the invention allows permits the determination of the quality of the liquid droplet or, in particular, the liquid spurt, in the light barrier unit when the temporal course of the sensor current during the shadowing of the light beam of the light barrier unit by the liquid droplet or spurt is recorded: In the case of spurt disturbances which can lead to incorrect metering, there are significant deviations in the expected signal waveform. This is illustrated, for example, in FIGS. 10A to 10C; which show different function-disturbed dosing channels. The parameter of the signal analysis according to the invention is in particular the temporal signal variation of the sensor signal, in particular at times during which the metered drops or spurts pass through the light barrier unit(s). A larger signal variance indicates a spurt disturbance, for example uneven spurt shape or spurt direction (intermittent spurt, wide spurt, deflected spurt) or uneven drop formation (too large, uneven or "breaking" drops).

In a preferred embodiment, each dosing channel, i.e. each needle or nozzle, of the microdispensing device is assigned to exactly one light barrier unit, consisting of a light source and a light sensor, which is directly assigned thereto. That is to say in particular in a multi-channel microdispensing device with several dosing channels arranged preferably in regular rows (one-dimensional array) or grids (two-dimensional array) a single light barrier unit consisting of a light source and a light sensor is directly assigned to each individual dosing channel. In this case, the light barrier units are arranged together on a common carrier, preferably a plurality of such light barrier units are arranged next to one another and preferably at regular intervals in a row or in a grid. The carrier is preferably arranged directly at the tips of the dosing channels, i.e. needles or nozzles, of the microdispensing device. This allows a compact and at the same time mechanically stable configuration of an integral "sensor plate" comprising a plurality of light barrier units arranged together on a common carrier. Preferably, the carrier or the carrier plate has window(s) where the liquid droplet or spurt emerging from the nozzle or needle can pass.

In a preferred embodiment, for each light barrier unit a beam-shaping aperture or screen is arranged between the light source and the light sensor for the purpose of shading of parts of the beam not required, primarily for improving the signal quality of the sensor signal. The aperture limits the light cone emanating from the light source to such an extent that a light cone which just covers the sensor surface of the light sensor, whereby the width of the light cone at the location of the discharged liquid is always broader than the width or dimension of the liquid droplet or spurt passing through (see FIG. 12). The aperture in this case may be designed as part of the housing or carrier, whereupon the light barrier unit is arranged in each case. This allows a compact and at the same time mechanically stable configuration of the integral "sensor plate".

Deviations from the ideal direction of the liquid drops or spurts in the direction of the axis of the light beam cannot be readily detected by a single intensity measurement. By intelligently comparing several measurements and by assuming that the predominant number of liquid drops or spurts are emitted in the ideal position, however, conclusions about mis-positioning also in the longitudinal direction of the light beam can be drawn. This is because, according to the invention, the light beam diverges and has a conical spreading. In a preferred embodiment though, the device has at least two independent light barrier units per each dosing channel, the light beams of which are at an angle to allow two spatial directions of the positional deviation of liquid drops or spurts to be detected more precisely. In this variant, two light barrier units are assigned directly to each dosing channel, at least two, preferably exactly two, light barrier units, the two light barrier units each consisting of one light source and one light sensor each. The two light barrier units are arranged relative to one another in such a way that their light beams, at least in the plane transverse to the propagation direction or ideal direction of the liquid drops or liquid spurts to be checked, are at an angle to one another. Preferably, the angle of the light beams relative to one another in this plane is approximately 90°, alternatively preferably approximately 60°. In further variants, the angle of the light beams to one another (in this plane) is approximately 30° to 150°, preferably 45° to 135°, more preferably 60° to 120°.

In a preferred embodiment, the device according to the invention contains for the purpose of evaluation and evaluation, in particular for controlling or regulating the dispensing behavior of the respective dosing channel of the microdispensing device, contains a programmed evaluation unit, which is at least connected to the respective light sensor and is suitable, by means of corresponding current-voltage converters and measuring amplifiers, high and/or bandpass filters, to produce a processed, conditioned and preferably temporally resolved signal representing the integrated intensity of the beam profile falling onto the respective sensor surface. Signal parameters for evaluation are the signal profile, i.e. pulse length, pulse amplitude, pulse slope, repetition rate, frequency spectrum, particularly high-frequency components, preferably determined via suitable filters or by Fourier transformation, and the statistical signal variance. The offset or bias, which can occur due to long-term drift at the sensors or misalignment of the light path on the light barrier units, can also be detected. This can be compensated, if necessary, by filters in the analog measuring chain and/or by sliding offset compensation.

The programmed evaluation unit preferably also contains a computing unit with a storage unit for determining and evaluating the temporal course of the light intensity on the sensor surface and/or for determining the difference of the intensity at the sensor surface once at the time of the liquid drop or liquid spurt passing through the light beam and once The time immediately before or after this event (undisturbed light beam).

Furthermore, the evaluation unit preferably has a signal or control device for signaling the deviation of the temporal intensity profile of the light intensity measured at the sensor from a predeterminable or pre-stored "ideal" intensity sequence and/or for signaling the deviation from a predeterminable, pre-stored intensity difference and/or for generation of an appropriate control signal, in particular for compensating a control deviation identified.

The evaluation unit, in particular in conjunction with the computing unit and the storage unit, is programmed in such a way that, for the purpose of checking the position of the liquid droplet or spurt emitted at the channels, Maximum stroke of the processed sensor signal, i.e. of the intensity profile, when the liquid droplet or spurt passes through the respective light beam, the ideal position of the liquid droplet or spurt, and a respective reduction of the amplitude deviation below a predeterminable threshold value indicates a deviation or directional change of the discharged liquid droplet or spurt from this ideal position.

Alternatively or additionally, the programmed evaluation unit, particularly in conjunction with the computing unit and storage unit, is programmed in such a way that, for the purpose of checking the quality of the liquid droplet or spurt delivered at the dosing channels according to the criteria described herein:

a maximum mean amplitude of the processed sensor signal, i.e. the intensity profile, during the liquid droplet or spurt passing the respective light beam of the light barrier unit and/or a minimal variance of the processed sensor signal, i.e. the intensity profile at this point of time indicate(s) the ideal quality of the liquid droplet or spurt, and a reduction in the amplitude to below a predeterminable threshold value or or a missing amplitude, or an increase in the variance of the processed sensor signal to above a predeterminable threshold value at the initiation of the delivery of the liquid droplet or spurt indicates a faulty dosing at the respective dosing channel on the microdispensing device.

In a preferred embodiment, the device according to the invention additionally has at least one signal return line, wherein the programmed evaluation unit, in particular via the signal or control device, is connected to an actuator on the microdispensing device for controlling the metering of the liquid droplet or spurt from the microdispensing device by means of preset values, which represent the ideal position or ideal quality of a dispensed liquid droplet or liquid spurt. Thus control is used for the automatic compensation of system-induced deviations of the liquid discharge at the respective dosing channels, needles or nozzles during operation by means of suitable actuators. Suitable actuating variables are amplitude and/or pressure at the respective actuator or metering head, which triggers the metering of liquid at the dosing channel. An alternative or additional accounting variable is the frequency of the release of the liquid discharge. An alternative or additional manipulated variable is the duration of the release of the liquid discharge. An alternative or additional actuating variable is the nozzle geometry. An alternative or additional actuating variable is a triggerable step for nozzle or needle cleaning, for example by means of additionally triggerable pressure waves, which possibly expel accumulated impurities or clogging from the nozzle or needle. Suitable actuators and actuators are preferably piezoelectric actuators, alternatively, electromagnetic actuators are preferred.

An essential aspect of the present invention is also the structurally simple integral construction of the respective light barrier units on a common carrier, which facilitates the cleanability, exchangeability and, at the same time, the precision of the measurement. As intended, complicated optical devices are dispensed with. The intelligent programming of the evaluation unit in conjunction with the light barrier unit with profiled light beam and integrating sensor surface provides a simple yet precise measuring instrument which reliably determines the quality of the liquid dosages at the respective dosing channels, and can compensate for this by means of a suitable return line.

This embodiment advantageously allows the provision of a fully autonomous, in particular self-adapting, microdispensing device, which allows an uninterrupted, fully automated dosing operation. This is of particular importance in plants for the automatic cultivation of cells and tissues in which sterilization by the operator should always be avoided by virtue of the sterility and purity to be adhered to, as well as the operating conditions to be observed, in particular ambient air, gassing and temperature. The optical control device according to the invention therefore permits the provision of multichannel microdispensing devices which can control and regulate small quantities of liquids, especially liquid drops or liquid spurts, in uninterrupted automated operation.

Accordingly, a further object of this invention is an improved multichannel microdispensing device for automatically metering liquid in the nanoliter or microliter range by means of recurring dispensing of liquid drops or small-volume liquid spurts suitable for uninterrupted automatic operation. This contains the optical control device of the present invention as an integral component, especially as an integral sensor plate arranged directly on the dosing channels, with a plurality of light barrier units supported on a common carrier.

The invention further provides a method for the controlled intermittent metering of liquid drops or liquid spurts to or by means of a multi-channel microdispensing device, in particular using the optical control device according to this invention. The method comprises at least the following steps: In a first step, a short-term dispensing of a liquid droplet or spurt of a small volume is triggered at the respective dosing channels, needles or nozzles of the microdispensing device.

In a further step, the light intensities of a light sensor with a sensor surface illuminated by a beam with an inhomogeneous profile, which is respectively assigned to the channels of the microdispensing device, are recorded over time as the liquid passes through the respective light beam. In a further step, an automatic evaluation of the light intensities takes place by means of the light intensities registered over time. In a further step, at least one control signal or warning signal is emitted, which serves for controlling the dispensing of the liquid from the microdispensing device in a closed control loop and/or for signaling an incorrect dosage of each channel of the microdispenser.

Object of the invention is thus particularly a method for the controlled delivery of liquid droplets or spurts from dosing channels of a multichannel microdispensing device, comprising the steps of:
  initiating a short-term output of a respective individual liquid drop or spurt to the dosing channels,
  illuminating the each discharge liquid droplet or spurt with a light beam having an inhomogeneous beam profile, and registering the respective attenuation of the intensity integrated over the width of the light beam when shaded through this liquid drop or spurt,
  automatically judging the respective registered dispensing-correlated intensity profile, and
  outputting a control or warning signal as a result of the evaluation for the purpose of controlling the dispensing of the liquid from the respective dosing channel and/or for signaling incorrect doses.

The evaluation is preferably carried out with the proviso that, that the mean maximum amplitude of the dispensing-correlated intensity attenuation for triggering delivery of the individual liquid drop or spurt the ideal dose indicating, whereas
  the reduction of the dispensing-correlated intensity attenuation below a predetermined threshold,
  the absence of a dispensing-correlated intensity attenuation, and/or
  the increase of the statistical signal variance of a dispensing-correlated intensity course profile over a predetermined threshold value
in each case indicates incorrect dosing on the respective dosing channel.

Preferably, for the control of the dispensing of liquid drops or spurts at each of the channels, that is particularly of its deviation from an ideal direction, it is provided that the maximum amplitude swing of the intensity signal at passage of the discharged liquid through the respective light beam indicates the ideal direction of the liquid droplet or spurt and a reduction in the amplitude, especially against an averaged maximum amplitude swing, indicates a deviation of the position or direction of the liquid drop or spurt.

In a variant, for the control of the quality of the discharged liquid droplet or spurt at each of the channels, i.e. particularly of its deviation from an ideal quality, it is provided that a deviation of the amplitude of the intensity signal when the discharged liquid passes through the respective light beam, in particular as compared to an averaged maximum amplitude, and in particular the temporal reduction in amplitude or a fluctuating signal or a temporary absence of an amplitude of the intensity at the initiation of the discharge, indicate(s) incorrect dosing at the respective channel.

DETAILED DESCRIPTION

Figure 1:
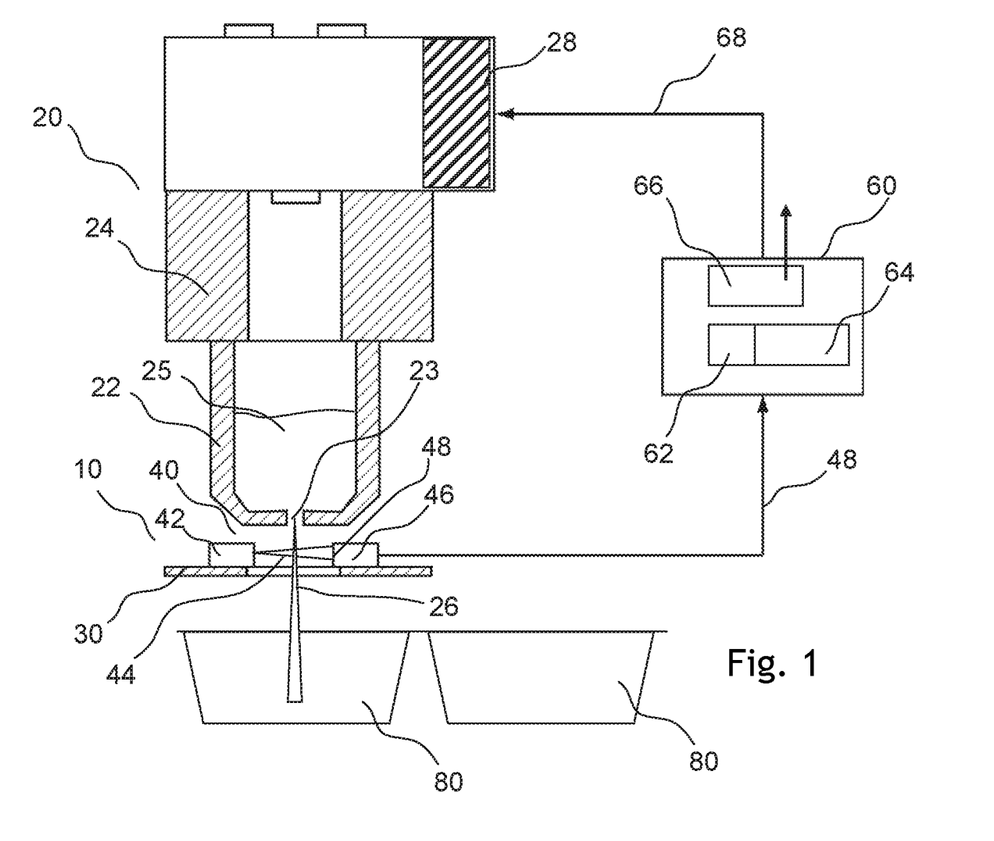
FIG. 1 is a schematic representation of the invention of the overall construction of a microdispensing device with an optical control device.

FIG. 1 is a schematic representation of the invention of the overall construction of a microdispensing device with an optical control device. For illustration, one of the several dosing channels is shown. The microdispensing device (20) has a driver or dosing head (24) per dosing channel (22). The metering head is adapted to apply recurrent pressure pulses to the supplied liquid (25) in the dosing channel (22) in order to expel the liquid from the nozzle (23). Immediately below the outlet or nozzle (23) of the dosing channel (22), the optical arrangement (10) according to the invention is positioned. This essentially consists of a supported light barrier unit (40) with a light source (42) for producing a shaped light beam (40) which projects onto the sensor surface (48) of a sensor (46). The light source (42) and sensor (46) together form the light barrier unit (40), which is provided at least once for each dosing channel (22) of the microdispensing device (20). The light barrier units (40) are arranged on the common carrier (30) and form the optical device (10) according to the invention, in particular in a multi-channel embodiment. The light beam (44) of the light barrier unit (40) is oriented in such a way that it is interrupted transversely by the liquid droplet or liquid spurt (26) which can be delivered from the microdispensing device (20). In this case, it is provided that the profiled light beam (44) is wider at this point, that is to say is more extensive, than the continuous liquid droplet or liquid spurt (26). The liquid droplet or spurt (26) preferably runs perpendicular in the vertical direction following the gravity vector. The liquid (25) releasable from the microdispensing unit (20) is dispensed into the trough or well (80), which preferably forms part of a microtiter or multi well plate having a plurality of troughs or wells (80) which are arranged regularly alongside one another. The signal of the sensor (46) of each light barrier unit (40) is fed via a respective line (48) to an evaluation unit (60) which is programmed such that the deviation of the light intensity on the sensor surface of the sensor (46) at passing of the liquid drop or spurt (26) can be used at the profiled light beam (44) for comparison with previously collected intensity values and/or for comparison with preset intensity values or temporal course of the intensity for assessing the dosing quality, the dosing direction, and/or mis-dosing. For this purpose, the programmed evaluation unit (60) preferably has a computing unit (64) with an associated storage unit (62) which stores the measured values of the light intensity. This is connected to a signal device (66) which is specifically adapted to signal the deviation from a predeterminable ideal value, in particular a predeterminable temporal intensity profile or predeterminable intensity difference, to an error dosing. Preferably, a return line (68) is provided, by means of which at least one control signal (actuating variable) is transmitted from the programmed evaluation unit (60) to at least one actuator (28) at the microdispensing device (20), which controls one or more parameters of the liquid metering of the respective dosing channel (22) and, in particular, automatically regulates it as a function of the detected quality of the liquid discharge. In the depicted embodiment, the actuator (28) is a pressure control device which determines the amplitude and frequency of the pressurization upon delivery of the liquid (25) from the dosing channel (22).

Figure 2:
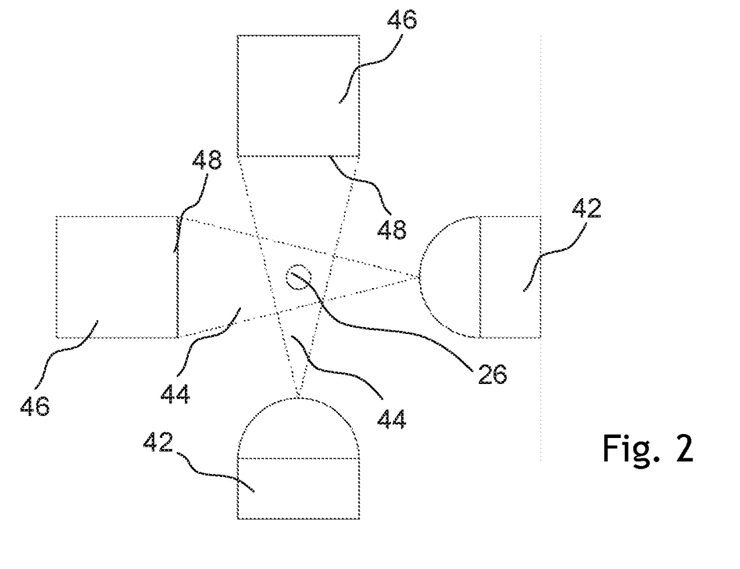
FIG. 2 is a schematic representation of a pair of light barrier units according to the invention in the viewing direction of the dispensed liquid.

FIG. 2 shows a schematic representation of a pair of light barrier units (40) according to the invention in the viewing direction of the dispensed liquid (26). A light source (42) in each case generates a beam cone (44) with an inhomogeneous, in particular Gaussian intensity profile, which is projected onto the sensor surface (48) of an Opposing sensor (46). Two light beams (44) extending substantially perpendicular to one another are formed together with a second light-barrier unit (40) identical thereto, for improved position determination of the continuous liquid droplet or spurt (26).

Figure 3:
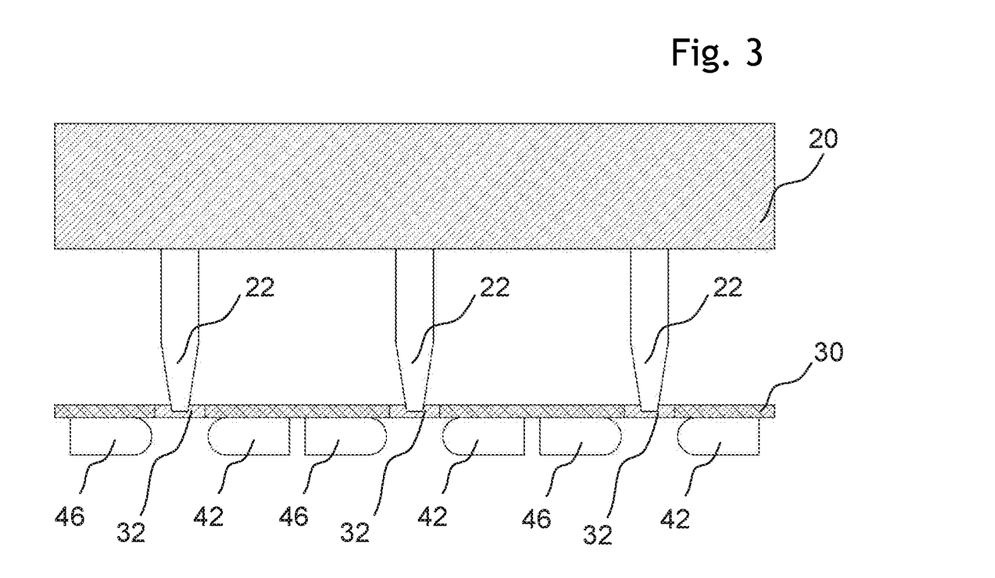
FIG. 3 and FIG. 4 each are schematic representations of specific embodiments of multi-channel microdispensing devices.
Figure 4:
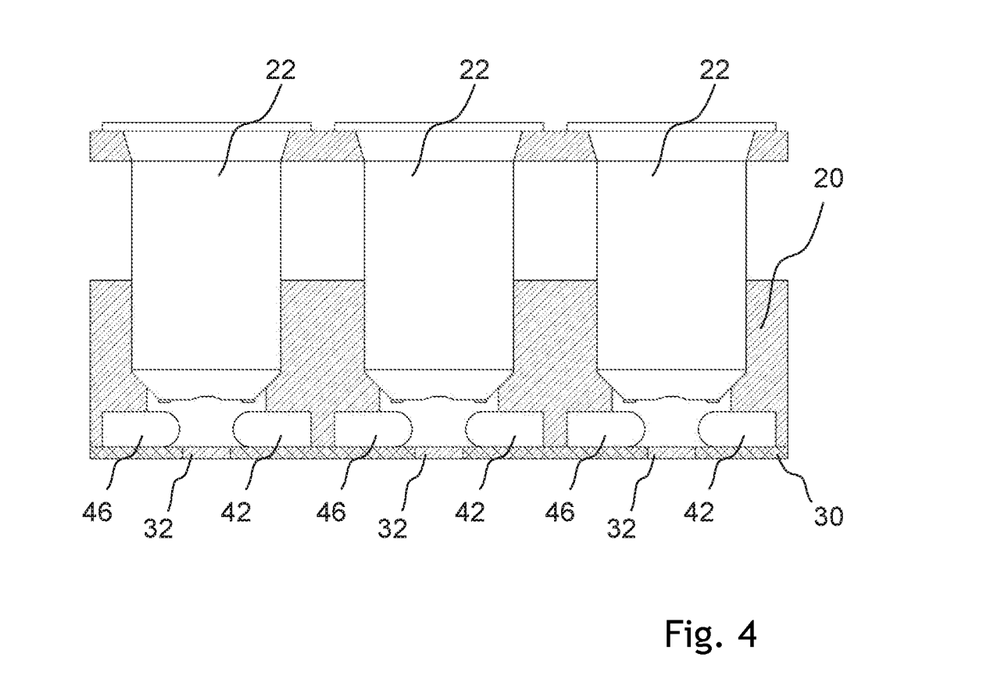

FIG. 3 and FIG. 4 each show schematic representations of specific embodiments of multi-channel microdispensing devices (20) each having a plurality of dosing channels (22) in the form of nozzles or needles which are parallel to one another in parallel. The at least one light barrier unit, consisting of the light source (42) and the light sensor (46), is arranged in each case on a carrier (30) directly at the tip of each dosing channel (22). In the illustrated embodiments, the carrier (30) is designed as a continuous plate which in each case has a window (32) at the points of passage of the dispensed liquid drops or spurts.

Figure 5A:
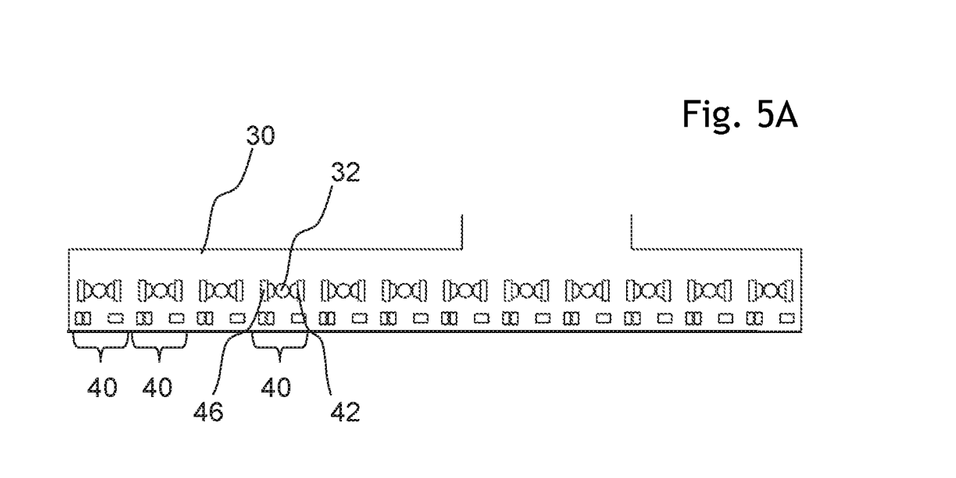
FIGS. 5A and 5B and FIG. 6 each show schematic top views of variants of devices according to the invention.
Figure 5B:
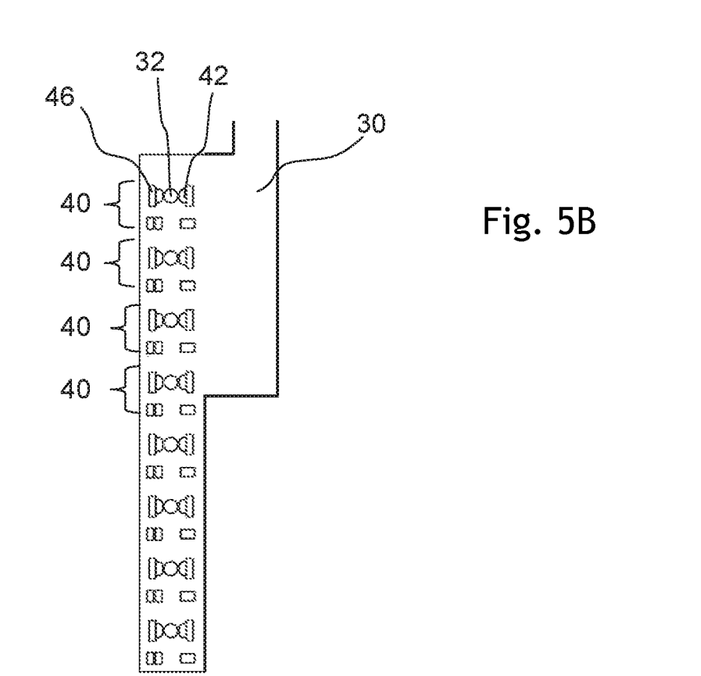
Figure 6:
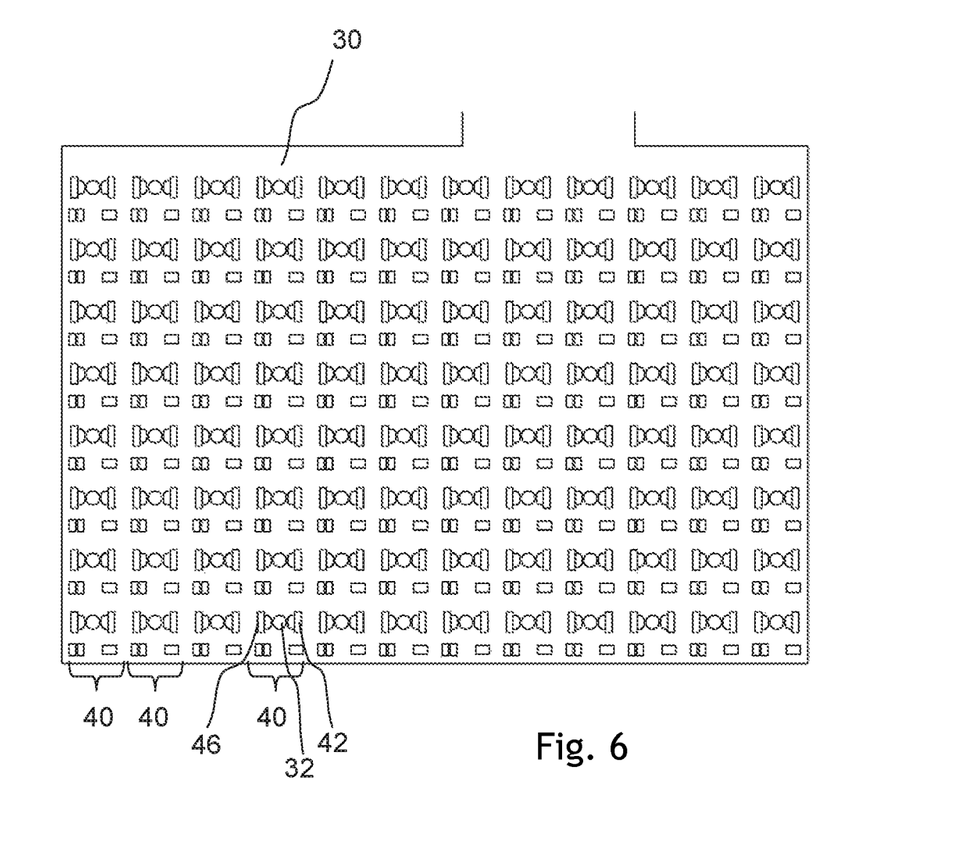
Figure 7A:
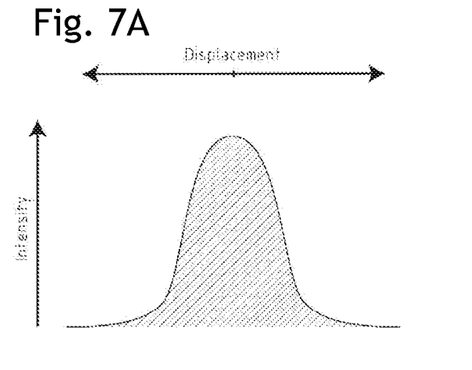
FIGS. 7A-7D show an intensity distribution in the beam profile of a shaped light beam of the device according to the invention along the cross-sectional line on the sensor surface of a light sensor.
Figure 7B:
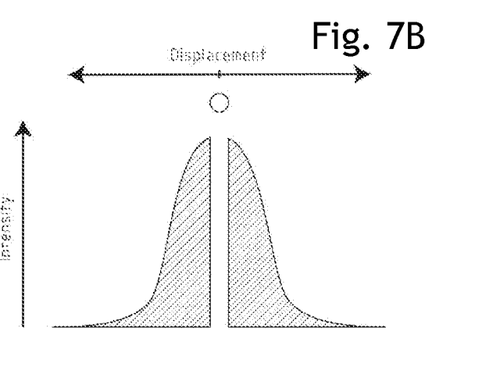
Figure 7C:
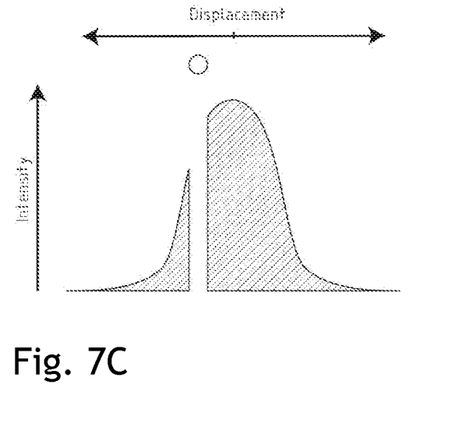
Figure 7D:
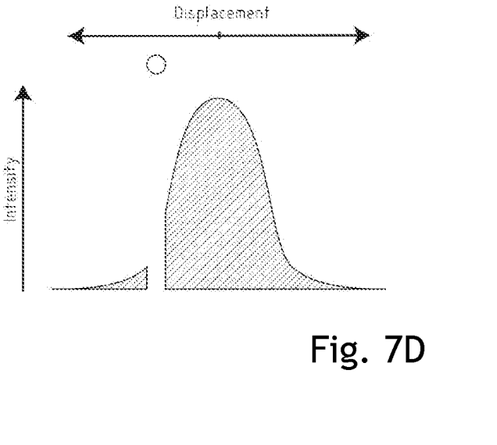

FIGS. 5A and 5B and FIG. 6 each show schematic top views of variants of devices according to the invention. In a preferred embodiment as integrated sensor plates with a plurality of light barrier units (40) which are parallel to each other and which are regularly interfered with one another, each consisting of a light source (43) and an associated light sensor (46), on a common carrier (30) and windows (32). For the passage of released liquid drops or spurts.

FIG. 7 shows an intensity distribution in the beam profile of a shaped light beam of the device according to the invention along the cross-sectional line on the sensor surface of a light sensor. Here, it is preferably provided in the sensor arrangement that the beam intensity is integrated over the entire width of the incident light cone. The measured light intensity corresponds to the integral below the area of the curve shown. In the case of an unbroken beam of light (no release of liquid or absence of liquid), the highest intensity of light is registered (FIG. 7A). The greatest attenuation of the intensity of the light is observed (FIG. 7B) when the liquid emitted flows through the profiled light beam precisely in the optical axis, i.e., centrally (=ideal position). With increasing deviation (displacement) of the liquid droplet out of the ideal position, the temporal shading, that is to say the intensity reduction when the liquid drop goes through the shaped light beam, is smaller (FIGS. 7C and 7D), which is used for position determination and quality assessment.

Figure 8:
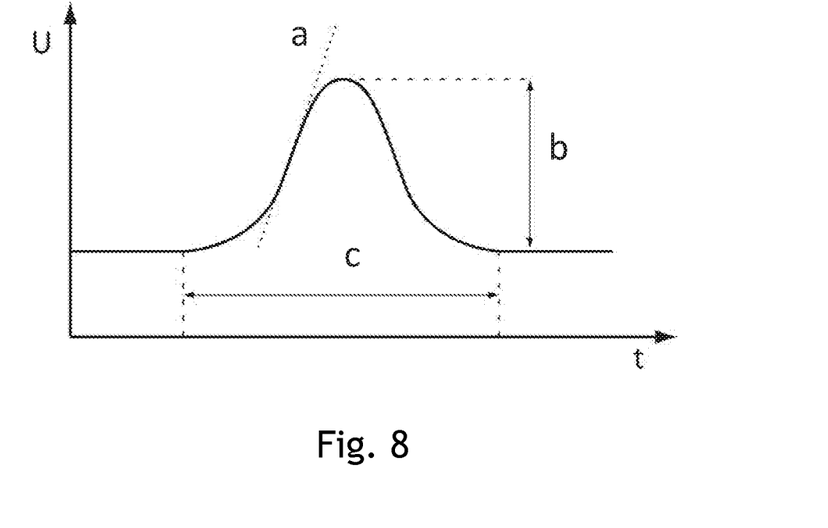
FIG. 8 graphically illustrates essential parameters employed in the programmed evaluation unit of the device according to the invention.
Figure 9A:
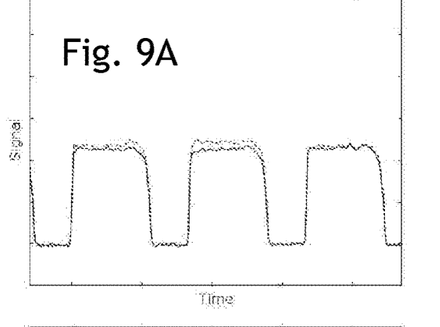
FIGS. 9A-9H graphically illustrate sensor signals of a pair of light barrier units on a dosing channel with light beams arranged essentially to one another at right angles.
Figure 9B:
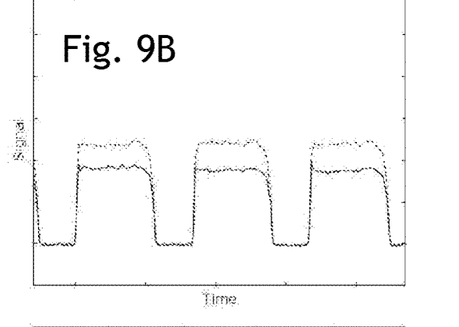
Figure 9C:
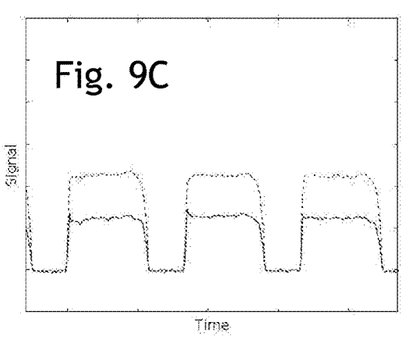
Figure 9D:
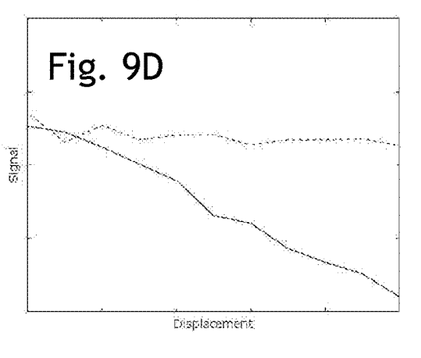
Figure 9E:
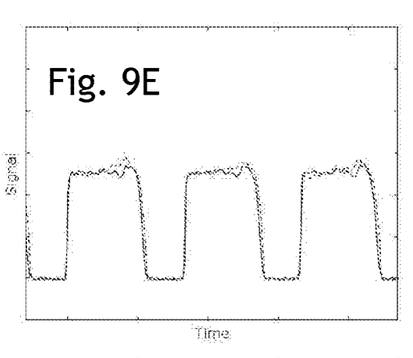
Figure 9F:
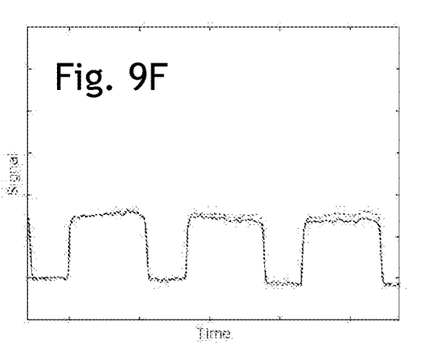
Figure 9G:
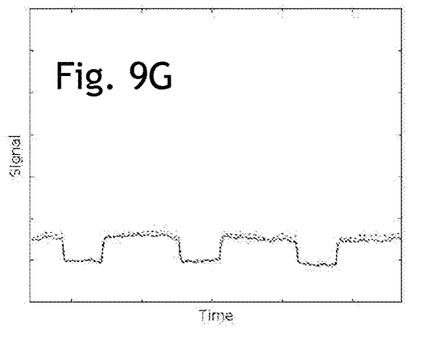
Figure 9H:
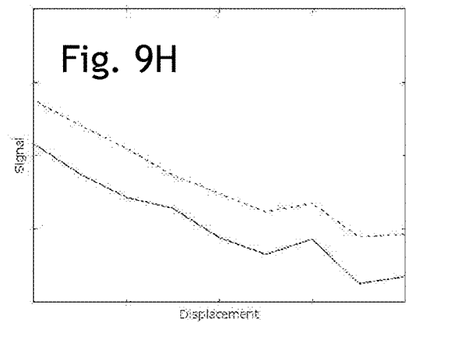

FIG. 8 shows essential parameters, which are employed in the programmed evaluation unit of the device according to the invention in the temporal course of the respective sensor signal to determine the quality of the liquid metering. The temporal course of the signal voltage is shown proportional to the inverted sensor current: A high voltage indicates a lower radiation intensity at the sensor surface. When the light beam breaks through the discharged liquid droplet or spurt, a voltage increase (a) noted gives an immediate indication of the quality of the liquid dosing, in particular when liquid spurts are discharged, the quality, in particular the uniformity of the liquid spurt, can be assessed. The height (b) of the signal amplitude, as shown in FIGS. 7A to 7D, particularly indicates the position of the dispensed liquid droplet or spurt. At the same time, if there is sufficient knowledge or assumption about the signal amplitude (b) of correct dosages in the ideal direction, other conclusions can be drawn about the quality of the liquid discharge. The course and the length (c) of the signal change, the type and the quality of the liquid discharge also indicate this.

FIG. 9 shows sensor signals of a pair of light barrier units on a dosing channel with light beams arranged essentially to one another at right angles (light barrier 1=continuous line, light barrier 2=dotted line). Measurement setup: Arrangement of the detection unit on an X-Y-Z table, which can be adjusted in three directions, below one dosing channel. Adjustment of the needle position to the optical axis took place by means of the shadow throw of the dosing needle. Needle was initially suspended in the light barrier—visible as a reduction in the sensor signal—and was then pulled up to the upper edge of the light cone of the light barrier. The signals show in each case a three-times triggered liquid emission with an ideal center crossing of the light beam (FIG. 9A) or when the liquid spurts are displaced from the ideal position, i.e. in the case of incorrect dosages (FIGS. 9B and C). FIG. 9D shows the dependency of the signal amplitude from the position or deflection of the liquid jet. FIGS. 9A to D show a situation when the liquid beam is displaced approximately 90°, i.e. transversely to the light beam of the first light barrier unit, and approximately 0°, i.e., along the optical axis light beam of the second light barrier unit. Although the liquid beam is shifted strictly along the longitudinal axis of a light beam of the second light barrier unit, a drop in the signal amplitude in the second unit (see dashed line) also occurs, as FIG. 9D shows. FIGS. 9E to H show the same test sequence with diagonal displacement deflection of the liquid jets about 45° to the light beam of the first light barrier unit and about 45° to the light beam of the second light barrier unit.

FIG. 10 shows measured electrical signals analogously to FIG. 9. FIG. 10A depicts an undisturbed ideal beam pattern of intermittently emitted liquid spurts. FIGS. 10B to C show various defective dosing channels, which spray differently. The quality, i.e., continuity and volume constancy of the metered liquid, decreases in FIGS. 10B and C. This suggests a mis-dosing. FIG. 10 D shows the dependency of the signal quality determined by means of the signal variance. The signal variability (in practice: noise on the peaks) is a decisive parameter for evaluating the beam quality.

Figure 11:
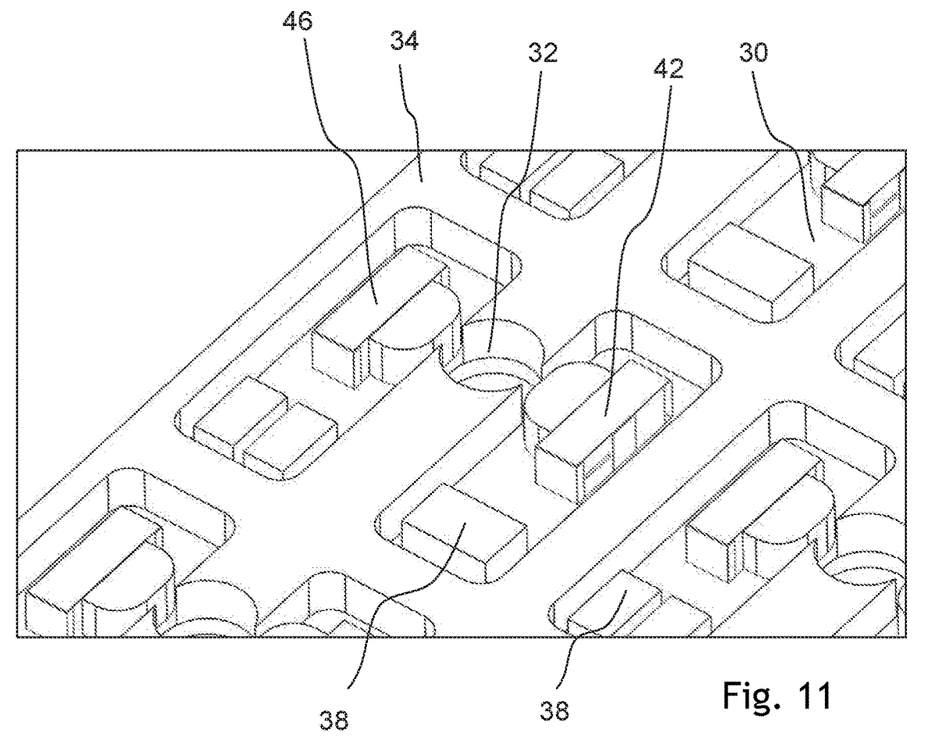
FIG. 11 is a schematic oblique view of a detail of the sensor plate according to the invention of FIG. 6.

FIG. 11 shows a schematic oblique view of a detail of the sensor plate according to the invention according to FIG. 6: On a carrier (30) which also corrects the electrical contacting and the printed tracks, light sources (42) with opposite light sensors (46) are attached in the form of SMDs. The carrier (30) contains further electronic components (38) for signal conditioning, which are applied as SMDs or are integrated in the carrier (30) in hybrid technology. In the depicted embodiment, the carrier (30) contains a carrier frame (34) with respective windows (32), where the liquid drops or spurts can pass through. The carrier frame (34) additionally serves as an aperture for beam shading in order to improve the signal quality at the sensor (46).

Figure 12:
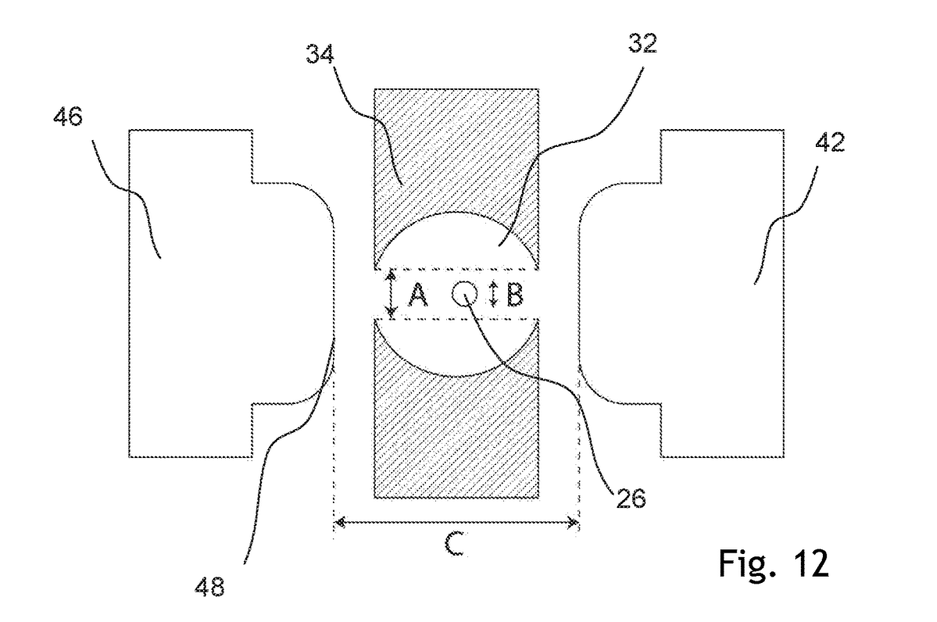
FIG. 12 is a schematic plan view of the arrangement according to FIGS. 5, 6 and 11.

FIG. 12 shows a schematic plan view of the arrangement according to FIGS. 5, 6 and 11 of a single light barrier unit consisting of the light source (42) and the opposing a sensor (46) with a sensor surface (48) and a carrier frame (34) with a window (32) through which the liquid droplet or spurt (26) can pass. The carrier frame (34) additionally serves as an aperture for beam shading in order to improve the signal quality at the sensor (46). The beam width (A) produced by the aperture is there always greater than the width (B) of the liquid droplet or spurt (26) passing through. Dimension A represents the aperture width. This is approximately 2 to 3 times the expected beam or drop diameter (dimension B). The sensor (46) and the LED light source (42) are mounted at a distance of approx. 2 to 4 mm. In a preferred embodiment as an integral sensor plate according to FIGS. 6 and 11 for the I-DOT microdispensing system, measure A is approximately 0.6 mm, in a preferred embodiment as an integral sensor plate according to FIG. 5A or B for a multidrop microdispensing system.

The invention claimed is:

1. A device for the optical control of liquid drops or spurts intermittently dispensed from a microdispensing device having a plurality of dosing channels, the device comprising:
    a plurality of light barrier units, each light barrier unit assigned to only a single associated dosing channel of the microdispensing device, each light barrier unit arranged directly with the single associated dosing channel on a common carrier and arranged regularly on the common carrier in a form of a grid (two-dimensional array) or a row (one-dimensional array) and form an integral sensor plate together with the common carrier, each light barrier unit including:
        a light source having an inhomogeneous beam profile; and
        a light sensor having a sensor surface onto which a profiled light beam of the light source projects,
    wherein each profiled light beam runs transversely with respect to a propagation direction of liquid drops or spurts dispensed from the microdispensing device and is wider than the liquid droplet or spurt to be controlled,
    wherein the dosing channel is a dosing needle or a dosing nozzle, and
    wherein the device includes a first number of light barrier units that matches a second number of dosing channels and each light barrier unit only measures droplets from the single dosing channel.

2. The device according to claim 1, further comprising:
    a programmed evaluation unit connected to a respective light sensor for determining an intensity of the profiled light beam as the profiled light beam contacts the sensor surface, and
    a storage unit and a computing unit for determining a temporal course of intensity and a difference in intensity at a time the liquid droplet or spurt passes and at an instance immediately before or after passing of the liquid droplet or spurt.

3. The device according to claim 2, further comprising:
    signal and control means for signaling a deviation from one of a predeterminable temporal course of intensity or an intensity difference.

4. The device according to claim 2, further comprising a signal return line connected to an actuator on the microdispensing device for controlling or regulating the dispensing of liquid from the respective dosing channel of the microdispensing device.

5. The device of claim 1 in combination with the microdispensing device having the plurality of dosing channels.

6. The device according to claim 1, wherein each light barrier unit comprises a first light source configured to emit a first light beam and a first light sensor configured to receive the first light beam and a second light source configured to emit a second light beam and a second light sensor configured to receive the second light beam.

7. The device according to claim 1, wherein each profiled light beam is a light cone having a highest intensity in an optical axis, in a center of the light bundle, which intensity drops in each case towards an edge of the light bundle,
    wherein the light sensor detects an entire beam profile of an incident light beam and integrates an intensity of the incident light beam over an extent of the incident light beam in a projection surface, a sensor current of the incident light beam corresponding to an integrated intensity;
    such that a maximum shading of the light beam, and a maximum reduction in sensor current occurs when the incident light beam is interrupted straight in a center of an optical axis of the incident light beam.

8. A device for the optical control of liquid drops or spurts intermittently dispensed from a microdispensing device having a plurality of dosing channels, the device comprising:
    a plurality of light barrier units arranged in at least one row on a carrier, each light barrier unit comprising:
        a light source configured to emit a light beam having an inhomogeneous beam profile, and
        a light sensor having a sensor surface onto which the light beam projects,
    wherein the device is positioned relative to the microdispensing device so that each light barrier unit is associated with only a single dosing channel of the plurality of dosing channels and when a liquid drop or spurt is dispensed from each single dosing channel, the liquid drop or spurt passes between the light source and the light sensor of the light barrier unit associated with the single dosing channel and through the light beam emitted by the light source,
    wherein each dosing channel is a dosing needle or a dosing nozzle, and wherein the device includes a first number of light barrier units that matches a second number of dosing channels and each light barrier unit only measures droplets from the single dosing channel.

9. The device according to claim 8, wherein the light beam has a width that is wider than a liquid drop or spurt that passes through the light beam.

10. The device according to claim 8, wherein the plurality of light barrier units are arranged in a plurality of rows defining a grid on the carrier.

11. The device according to claim 8, further comprising a second plurality of second light barrier units arranged on the carrier, each second light barrier unit comprising:
   a second light source configured to emit a second light beam, and
   a second light sensor configured to receive the second light beam,
   wherein each second light barrier unit is positioned relative to one of the light barrier units so that the light beam and the second light beam cross at an angle of about 30° to about 150° and when a liquid drop or spurt is dispensed from each single dosing channel, the liquid drop or spurt passes through the light beam and the second light beam.

12. The device according to claim 8, wherein each light barrier unit comprises a first light source configured to emit a first light beam and a first light sensor configured to receive the first light beam and a second light source configured to emit a second light beam and a second light sensor configured to receive the second light beam.

13. The device according to claim 8, wherein each light beam is a light cone having a highest intensity in an optical axis, in a center of the light bundle, which intensity drops in each case towards an edge of the light bundle,
   wherein the light sensor detects an entire beam profile of an incident light beam and integrates an intensity of the incident light beam over an extent of the incident light beam in a projection surface, a sensor current of the incident light beam corresponding to an integrated intensity;
   such that a maximum shading of the light beam, and a maximum reduction in sensor current occurs when the incident light beam is interrupted straight in a center of an optical axis of the incident light beam.

14. A microdispensing device comprising:
   a plurality of dosing channels; and
   a plurality of light barrier units arranged in at least one row on a carrier, each light barrier unit comprising:
      a light source configured to emit a light beam having an inhomogeneous beam profile; and
      a light sensor having a sensor surface onto which the light beam projects,
   wherein the plurality of light barrier units are positioned relative to the plurality of dosing channels so that each light barrier unit is associated with only a single dosing channel of the plurality of dosing channels and when a liquid drop or spurt is dispensed from each single dosing channel, the liquid drop or spurt passes between the light source and the light sensor of each light barrier unit and through the light beam emitted by the light source,
   wherein the dosing channel is a dosing needle or a dosing nozzle, and
   wherein the device includes a first number of light barrier units that matches a second number of dosing channels and each light barrier unit only measures droplets from the single dosing channel.

15. The device according to claim 14, wherein each light barrier unit comprises a first light source configured to emit a first light beam and a first light sensor configured to receive the first light beam and a second light source configured to emit a second light beam and a second light sensor configured to receive the second light beam.

16. The device according to claim 15, wherein the first light source and the second light source are arranged so that the first light beam and the second light beam have an angle relative to one another of from 30° to 150°.

17. The device according to claim 14, wherein the each light barrier unit is fixedly associated with only a single dosing channel of the plurality of dosing channels.

18. The device according to claim 14, wherein each dosing channel of the plurality is configured to supply a single liquid.

19. The device according to claim 14, wherein each light beam is a light cone having a highest intensity in an optical axis, in a center of the light bundle, which intensity drops in each case towards an edge of the light bundle,
   wherein the light sensor detects an entire beam profile of an incident light beam and integrates an intensity of the incident light beam over an extent of the incident light beam in a projection surface, a sensor current of the incident light beam corresponding to an integrated intensity;
   such that a maximum shading of the light beam, and a maximum reduction in sensor current occurs when the incident light beam is interrupted straight in a center of an optical axis of the incident light beam.

20. A device for the optical control of liquid drops or spurts which are intermittently dispensed from a microdispensing device, the device comprising:
   at least one light barrier unit assigned to only a single associated dosing channel of the microdispensing device, each light barrier unit arranged directly with the single associated dosing channel on a common carrier, each light barrier unit including:
      a light source having an inhomogeneous beam profile; and
      a light sensor having a sensor surface onto which the profiled light beam of the light source projects,
   wherein a profiled light beam for each light barrier unit runs transversely with respect to a propagation direction of dispensed liquid drops or spurts and is wider than the liquid drops or spurts to be controlled,
   wherein each profiled light beam is a light cone having a highest intensity in an optical axis, in a center of the light bundle, which intensity drops in each case towards an edge of the light bundle,
   wherein the light sensor detects an entire beam profile of an incident light beam and integrates an intensity of the incident light beam over an extent of the incident light beam in a projection surface, a sensor current of the incident light beam corresponding to an integrated intensity such that a maximum shading of the light beam and a maximum reduction in sensor current occurs when the incident light beam is interrupted straight in an optical axis center of the incident light beam.

* * * * *